(12) United States Patent
Brady et al.

(10) Patent No.: US 6,999,883 B1
(45) Date of Patent: Feb. 14, 2006

(54) LANDFILL GAS EXTRACTION CONSTANT FLOW CONTROL METHOD AND DEVICE

(76) Inventors: John Brady, 2599 Quail La., Los Osos, CA (US) 93402; Greg S. Powell, 109 Calle Propano, #B, Paso Robles, CA (US) 93446; Robin Marks, 548 Hill St., San Luis Obispo, CA (US) 93405

( * ) Notice: Subject to any disclaimer, the term of this patent is extended or adjusted under 35 U.S.C. 154(b) by 0 days.

(21) Appl. No.: 10/710,721

(22) Filed: Jul. 29, 2004

Related U.S. Application Data

(63) Continuation-in-part of application No. 10/098,672, filed on Mar. 15, 2002, now abandoned.

(51) Int. Cl.
*G01L 7/00* (2006.01)
*G01N 11/00* (2006.01)

(52) U.S. Cl. .................................................. 702/50

(58) Field of Classification Search .................. None
See application file for complete search history.

(56) References Cited

U.S. PATENT DOCUMENTS

| | | | |
|---|---|---|---|
| 4,026,355 A | 5/1977 | Johnson et al. | 166/246 |
| 4,890,672 A | 1/1990 | Hall | 166/250 |
| 6,169,962 B1 | 1/2001 | Brookshire et al. | 702/47 |

*Primary Examiner*—Michael Nghiem
(74) *Attorney, Agent, or Firm*—William Keyworth; Bill & Mary Lou Inc.

(57) ABSTRACT

A control method and apparatus for regulating gas flow from landfill gas wells uses a differential pressure-regulating valve to maintain a set flow through a constant flow wellhead assembly. This wellhead assembly maintains a constant flow from the well despite normal variations in environmental factors affecting gas flow. The wellhead assembly includes a second valve that is used in series with the pressure-regulating valve to adjust the operating conditions of the regulating valve to keep it within its operating range. The pressure-regulating valve configuration allows a simple automatic control to position the valve. Periodic manual sampling of extracted gas and adjustment of the valve conditions is used to adjust for longer-term variations in well conditions.

18 Claims, 7 Drawing Sheets

Fig. 5B

LANDFILL GAS EXTRACTION CONSTANT FLOW CONTROL METHOD AND DEVICE

CROSS REFERENCE TO RELATED APPLICATIONS

This application is a continuation-in-part of U.S. Nonprovisional patent application Ser. No. 10/098,672 "Landfill Gas Extraction Constant Flow Control Method and Device" filed on Mar. 15, 2002 now abandoned, which is incorporated herein by reference.

FEDERAL RESEARCH STATEMENT

Not applicable

BACKGROUND OF INVENTION

1. Field of the Invention

This invention relates to a control method and apparatus for optimizing the extraction of decomposition gas from solid waste landfills. More specifically, the present inventions pertains to a method using a wellhead device that when installed and operated on a landfill gas extraction well will provide the capability to select and maintain a constant flow rate of gas extraction from the subsurface. This capability allows controlling the extraction at near the gas generation rate for the well. The device also includes a high temperature shutdown feature in which the wellhead will stop gas extraction from the well for the purposes of minimizing the potential or exasperation of subsurface fires.

2. Description of Related Art

Once municipal solid waste is disposed of at a landfill, the organic fraction of the waste begins to decompose. This decomposition first proceeds through an aerobic biodegradation process where all the available oxygen in the buried waste is consumed. The decomposition then proceeds through a strictly anaerobic biodegradation process where the principle constituents of landfill gas are formed. Landfill gas consists of approximately 55% methane, 44% carbon dioxide and less than 1% trace gases. The trace gases consist of a wide variety of volatile organic compounds, which vary depending on the particular landfill. Noteworthy is the fact that oxygen is toxic to the microorganisms typically responsible for methane gas generation.

Since landfill gas is constantly being produced as a result of waste decomposition, landfill gas will move from the buried waste towards the ground surface and will result in surface emissions to the atmosphere. The constant generation of landfill gas also results in a flushing or purging action within the subsurface that results in the removal of air, thus further facilitating the anaerobic biodegradation process.

Surface emissions of landfill gas is not a desirable condition because the primary constituents of landfill gas are well known green house gases, which are thought to be contributing towards global warming. In addition, the trace gases present in landfill gas are believed to participate in an atmospheric photochemical reaction that leads to the formation of ozone, a principle constituent of smog.

In addition to surface emissions, landfill gas may also move or migrate laterally in the subsurface away from the buried decomposing waste, and may accumulate in near-by buildings or other structures. This condition creates a potentially dangerous condition due to the methane content of landfill gas. When methane is present in a concentration ranging from approximately 5 to 20 percent by volume it is potentially explosive. Another issue associated with subsurface migration of landfill gas is that it may also come into contact with groundwater and create the potential for groundwater contamination due to the presence of contaminating trace gases.

Thus it is desirable to collect landfill gas to prevent these negative environmental effects. It is also desirable to collect landfill gas for energy recovery purposes, as the methane content of landfill gas can be relatively easily used as a fuel.

Active landfill gas well extraction systems are used to control landfill gas surface emissions, control landfill gas subsurface migration away from the landfill, and often to collect landfill gas for energy recovery. These systems typically include an array of both vertical and horizontal landfill gas extraction wells that are in fluid communication with a common header piping system. The header piping system is, in turn, fluidly connected to a vacuum source, typically a centrifugal blower or other similar turbo-machine. Following extraction by the system, the gas may be incinerated by a flare, may be directly used as a fuel, or may be conditioned and then used as a fuel.

The landfill extraction system wells are either drilled or trenched into the landfill waste column and they consist of both perforated-piping sections and solid-piping sections. The solid piping section is nearest the surface of the landfill. The perforated-piping section is the deeper piping. The point at which the solid piping changes to perforated piping is a major design consideration for an extraction well, since it significantly influences the maximum allowable suction that can be applied to each well.

Each extraction well is in fluid communication with a header piping system through a wellhead assembly. The wellhead assembly typically consists of a gate valve used for throttling the volumetric flow rate of landfill gas from the extraction well and a sample collection port. The wellhead may also include a flow rate measurement device.

An operating goal of the landfill gas well extraction system is to remove gas at the approximate rate of its generation. The rational for this goal is the consequence of over- or under-extraction rates. Under-extraction rates mean the extraction rate is not high enough to prevent gas from reaching the surface or prevent subsurface migration. This results in air pollution, or a fire hazard. Over-extraction rates mean the extraction rate is high enough to draw large amounts of air into the waste column. This may cause a subsurface fire, and will kill many of the microorganisms responsible for the formation of methane, resulting in reduced methane recovery. Consequently, the gas flow rate from each individual extraction well, or group of adjacent wells, needs to be carefully monitored and controlled within a narrow operating range to prevent over- or under-extraction of landfill gas.

Several factors are involved in causing short-term over- or under-extraction rates in present extraction systems. Extraction systems typically rely upon one common vacuum source that is in fluid communication with the header piping system for all the wells. A centrifugal blower or similar turbo-machine is most commonly used as a vacuum source, although reciprocating compressors have also been used. The efficiency of turbo-machines is affected by gas temperature, which results in a variation in the mass flow rate developed by the turbo-machine with changes in temperature. This temperature-caused flow variation is reflected in a variation of the extraction rate at each of the system wells. The gas temperature changes with ambient temperature that, in turn varies over the course of a day, resulting in a diurnal variation. Landfill gas is alternately diluted and concentrated as a result of this mass flow rate variation. The magnitude of the effect depends upon the magnitude of the mass flow variation of the turbo-machine and the individual well construction characteristics.

Changing barometric pressures is another factor affecting extraction rates. Variations in atmospheric pressure modify the over-all resistance to flow in the extraction well and header piping system.

Changes in the landfill surface topology, such as differential settlement of the landfill surface, the development of landfill surface cracks, or waste separation from side slopes of the landfill may change the flow characteristics of the extraction system. These may cause a lower resistance to flow than an intact surface resulting in a short-circuit flow of air into the extraction system resulting in large quantities of air being drawn into the subsurface.

All of these effects result in a continuous cycle of over and under extraction of landfill gas by the extraction system. Methods to control these cycles have been proposed. U.S. Pat. No. 4,026,355 (Johnson et al.) describes a control method using various measurements of pressure within the landfill. This method has the drawback of requiring precise subterranean pressure measurements in the landfill that involve remote data communication. Such remote measurements in a landfill environment are subject to a variety of malfunctions from natural and man-made causes. U.S. Pat. No. 4,890,672 (Hall) describes a control method using measurement of the extracted gas temperature. This method is based on correcting an over-extraction by measuring its consequences, rather than controlling to prevent over-extraction. U.S. Pat. No. 6,169,962 (Brookshire et al.) describes a complex and extensive computer-controlled system and computer program involving using a wide variety of parameters to determine the control signal for the control valves in the extraction system. This system requires an expensive instrumentation and control system, and the communications for a remote control computer, which again is subject to malfunctions in a landfill environment.

What is needed is a simple, rugged, inexpensive control method and system that is based on the causes of landfill gas extraction system over- or under-extraction rates.

SUMMARY OF INVENTION

The present invention is a constant flow control wellhead assembly for a landfill gas well extraction system. The system includes a manually controlled valve that can be positioned open, closed, or in any position in between. The manually controlled valve is connected such that all flow from the well passes through the valve. A pressure-regulating valve is connected upstream of the manual valve such that all flow from the well also passes through this valve. A pressure tap in the piping upstream of the pressure-regulating valve and a pressure tap in the piping between the manually controlled valve and the pressure-regulating valve are installed to measure the differential pressure across the pressure-regulating valve. Another pressure measurement tap in the piping downstream of the manually controlled valve is installed so the differential pressure across the entire wellhead assembly may be measured. A sample tap is also installed upstream of the pressure-regulating valve to sample the landfill gas passing through the wellhead, and an electronic display and control circuit is provided so the differential pressure across the pressure-regulating valve may be displayed to set the desired position of the manually controlled valve, and the differential pressure across the entire wellhead assembly may be displayed and used as a control parameter for the pressure-regulating valve.

The constant flow control wellhead is used by installing the system in a section of piping between each well, or grouping of wells with a single extraction pipe, and the well extraction vacuum source. The differential pressure-regulating valve in the wellhead gas path is initially opened to a nominal position that corresponds to a unique flow rate, and the manual valve is also partially opened. The differential pressure across the differential pressure-regulating valve is measured, and the manual valve position adjusted to set the desired differential pressure across the differential pressure-regulating valve. The nominal position of the differential pressure-regulating valve and the desired differential pressure together creates a unique flow rate through the wellhead assembly. The flow rate is controlled by the differential pressure across the complete wellhead assembly. The differential pressure equivalent to the entire flow through the wellhead assembly is measured, and the differential pressure-regulating valve position is adjusted automatically as needed to maintain this desired differential pressure. The gas composition of each landfill gas well is measured on a periodic basis, and the gas composition is evaluated to determine if the flow rate from the landfill gas extraction well should be modified to prevent long term over or under extraction. The flow adjustment is done by again adjusting the position of the differential pressure-regulating valve, then measuring the adjusted differential pressure across the differential pressure-regulating valve, followed by adjusting the position of the manual valve to obtain the desired differential pressure across the differential pressure-regulating valve, then measuring the adjusted differential pressure equivalent to the entire flow through the wellhead assembly, and adjusting the regulating valve position automatically, as needed, to maintain this desired differential pressure.

OBJECTS AND ADVANTAGES

One object of this invention is to provide a landfill gas extraction control method and apparatus that will control short-term fluctuations in extraction flow that can lead to over- or under-extraction of gas.

A second object of this invention is to provide a landfill gas extraction control method and apparatus that requires minimal supervision.

A third object of this invention is to provide a landfill gas extraction control method and apparatus that is low in installation and maintenance cost.

A fourth object of this invention is to provide a landfill gas extraction control method and apparatus that will provide a shutdown of the gas extraction if dangerously high extraction temperatures occur.

BRIEF DESCRIPTION OF DRAWINGS

A more complete understanding of the invention can be obtained by considering the detailed description in conjunction with the accompanying drawings, in which.

REFERENCE NUMERALS IN DRAWINGS

These reference numbers are used in the drawings to refer to area or features of the methane gas extraction constant flow wellhead.
50 Manual Flow Regulating and Shut-off Valve
51 Manual Valve Handle
52 Differential Pressure-Regulating Valve
54 Upstream Pressure Measurement Tap
55 Intermediate Pressure Measurement Tap
56 Downstream Pressure Measurement Tap
58 Temperature Sensor
60 Sample Collection Port
62 Control Section Housing
64 Control Circuit 66 Data Port
70 Differential Pressure Regulating Valve Flow Area
72 Differential Pressure Regulating Valve Flap
74 Differential Pressure Adjustment Valve Stem
76 Differential Pressure Regulating Valve Stepper Motor
78 Differential Pressure Regulating Valve Flap Position Sensor
80 Differential Pressure Regulating Valve Body and Bonnet
82 Wellhead Piping
100 Well Extraction Pipe
102 Pipe to Well Extraction Vacuum Source
104 Data Port
106 Battery
108 Straight Lower Edge of the Flap
120 Methane Gas Extraction Constant Flow Control Wellhead Assembly
130 Flow Measurement Device

DETAILED DESCRIPTION

The principle of operation of the present invention is based on well-known fluid dynamic considerations. The first law of thermodynamics general energy equation can be used to relate the pressure loss resulting from fluid flow within a piping system to a specific flow rate. In flow rate measurement a restriction within a pipe is constructed which reduces the cross-sectional area of the pipe's traverse plane with respect to fluid flow. The pressure difference measured at the upstream and down streamside of the restriction, known as differential pressure, is used to determine the flow rate of the fluid. The unique flow rate is also dependant upon the cross sectional area of the restriction, the geometry of the piping system up and downstream of the restriction, as well as the fluid characteristics.

Figure 1:
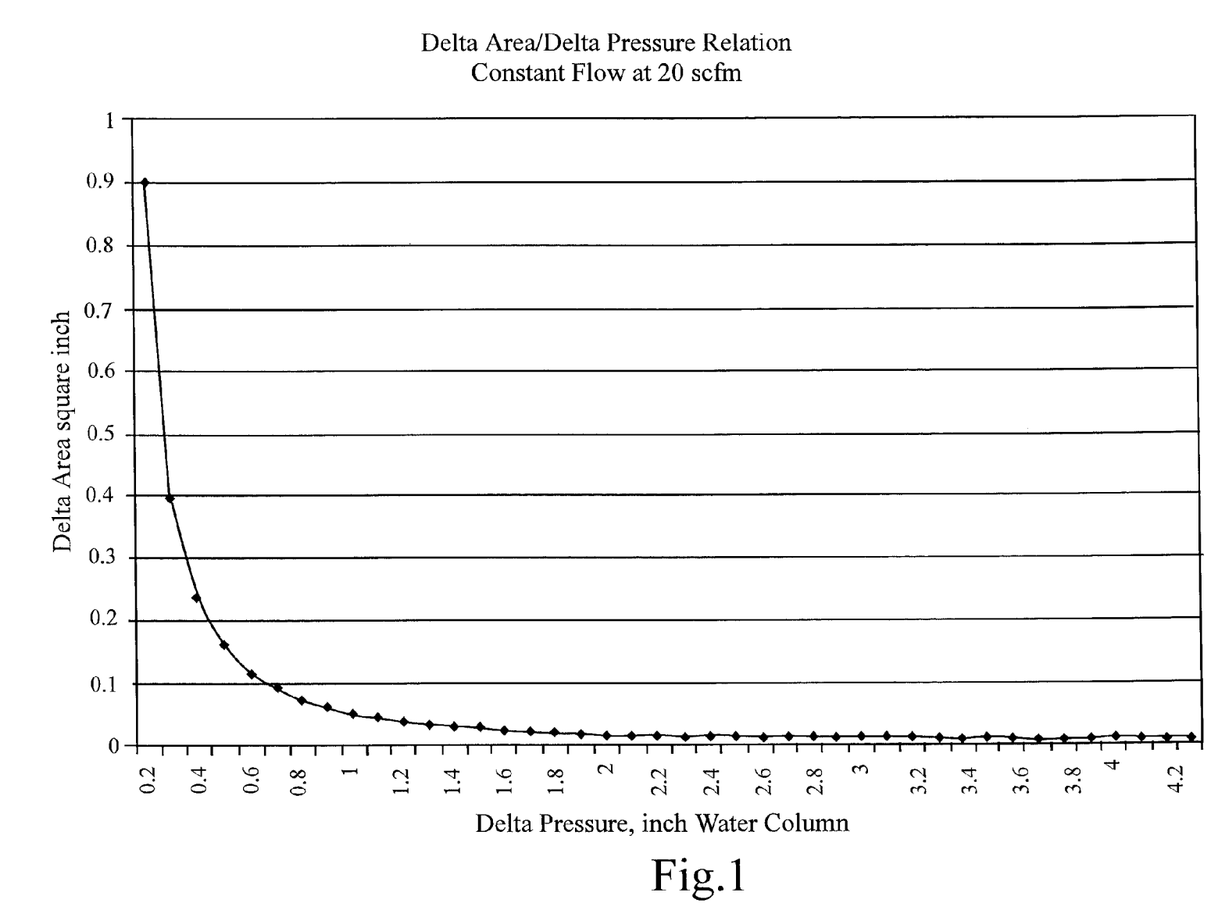
FIG. 1 is a graph of the relationship of the area of a typical landfill gas flow restriction and the differential pressure across the flow restriction at a constant flow rate.

In a situation where the flow rate, gas characteristics, and pipe geometry are held constant, an inter-relationship will exist between cross sectional area of the restriction and the pressure difference across the restriction. A range of paired values of these parameters is possible in which the flow rate is constant, as illustrated by FIG. 1, which uses a flow rate of 20 scfm. This principle is exploited in the present invention through using it as a basis for a highly effective throttling valve, known as the differential pressure-regulating valve. Throttling is the positioning of the valve to provide a particular flow restriction.

There is a range of differential pressures that approximate a linear relationship with the flow area for a given constant flow rate. FIG. 1 shows this linearity approximation in the range 1 to 4 inches water column (WC). Lower differential pressures than this are non-linear, requiring larger and larger changes in flow area for a given change in differential pressure. Conversely at higher differential pressures the change in differential pressure becomes larger for a given change in flow area such that control becomes very difficult. In this linear range, maintaining a constant flow rate involves changing the flow area a given amount for a given change in differential pressure. Since the required change in flow area varies over the linear range, the differential pressure-regulating valve internals provide increased changes in flow area as the valve is opened.

The flow control section of the wellhead assembly is designed to maintain a constant gas flow by varying the available cross sectional area of the differential pressure-regulating valve so gas flow will respond to changes in fluid conditions external to the wellhead assembly. These changes manifest themselves as changes in the differential pressure equivalent to the entire flow through the wellhead assembly.

Figure 3:
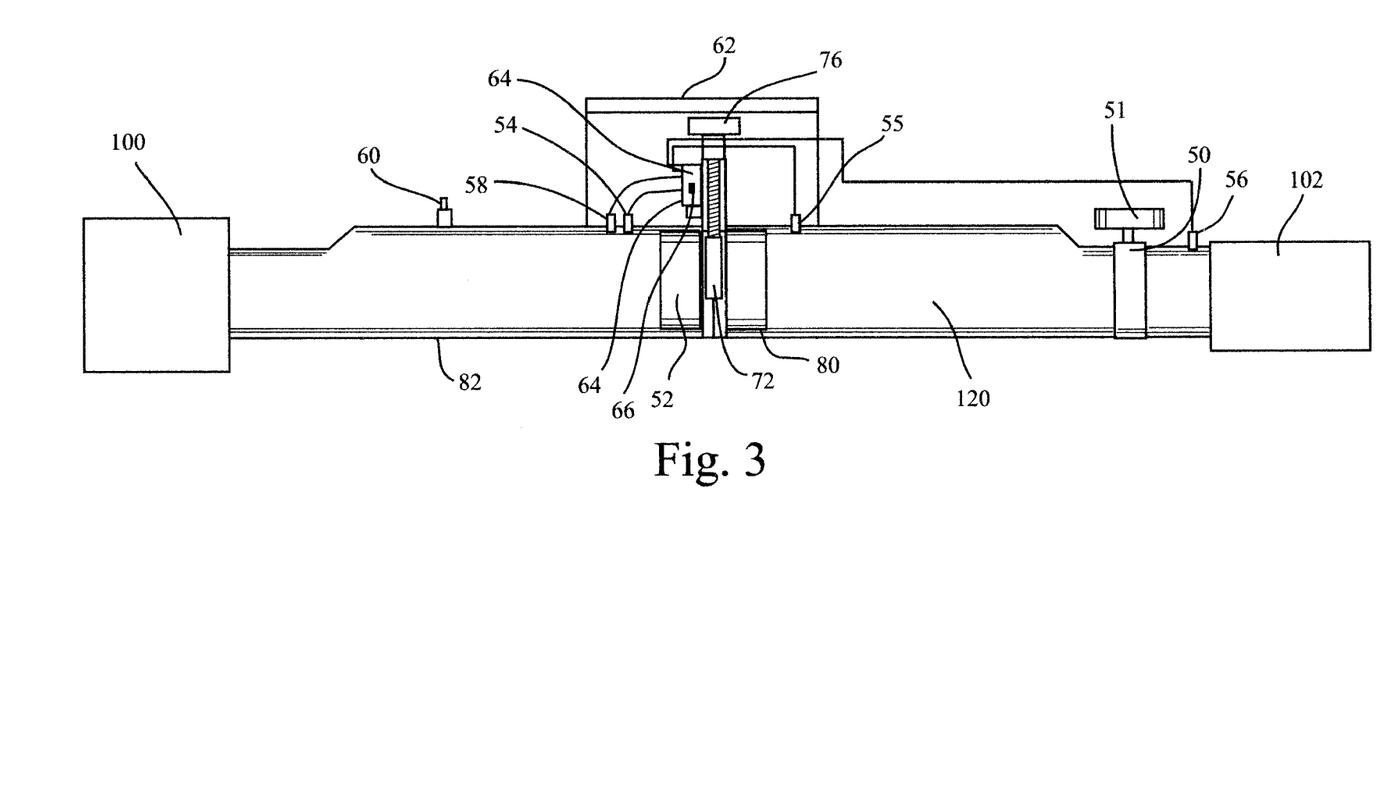
FIG. 3 shows the arrangement of the methane gas extraction constant flow control wellhead assembly.
Figure 5A:
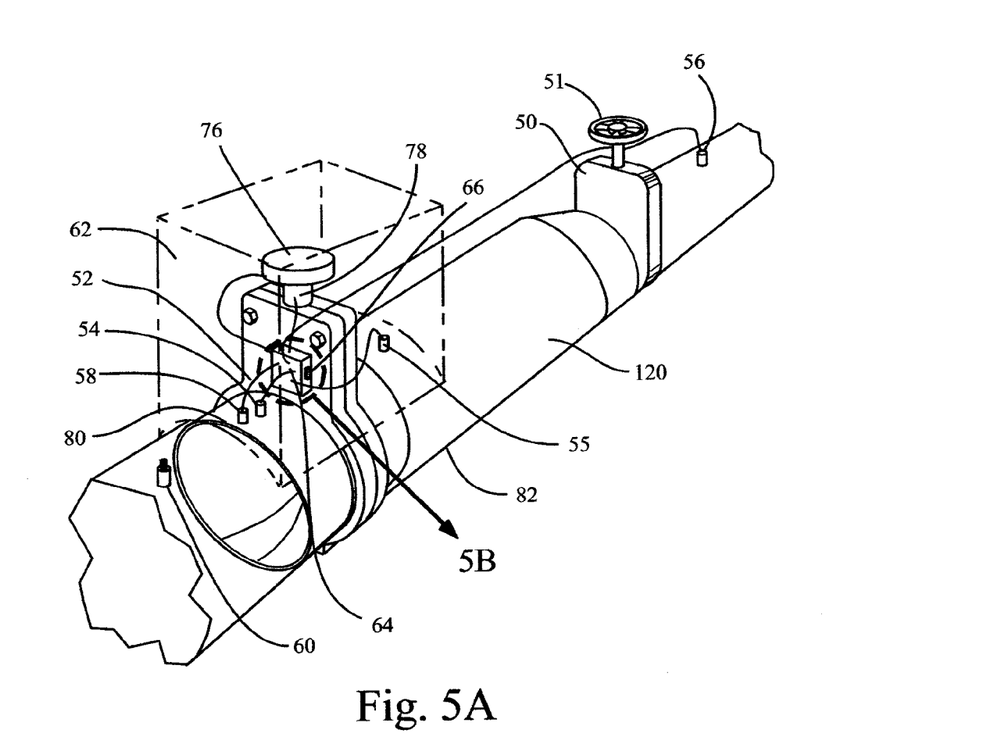
FIG. 5A is an isometric view of the methane gas extraction constant flow control wellhead assembly.

The complete wellhead assembly gas path includes the flow control components as shown in FIGS. 3 and 5A, and consists of a manual flow regulating and shut-off valve (50), an automatically adjusting differential pressure-regulating valve (52), arranged in series in the flow path from a well, and pressure sensing taps (54, 55, 56). The flow is controlled at the desired flow rate through action of the differential pressure-regulating valve, which throttles the gas flow to achieve a constant differential pressure equivalent to the entire flow through the wellhead assembly. The differential pressure across the complete wellhead assembly gas path is the equivalent of the entire flow through the wellhead assembly. The complete wellhead assembly differential pressure is the difference in pressure measurements between the inlet to the differential pressure-regulating valve and the outlet of manual flow regulating and shut-off valve as measured at the upstream pressure tap (54) and the downstream pressure tap (56). This differential pressure is equivalent to the entire flow through the wellhead assembly and is used as the operating control parameter for the pressure-regulating valve. Maintaining the differential pressure across the complete wellhead assembly gas path at the desired operating control point assures a constant flow rate.

The differential pressure-regulating valve (52) maintains the constant flow rate through movement of the differential pressure-regulating valve flap (72) to vary the throttling of the gas flow. The manual flow regulating and shut-off valve (50) is adjusted by turning the valve handle (51) when the wellhead is placed in service to maintain the differential pressure in the range of 1 to 4 inches water column (WC) across the differential pressure-regulating valve, as measured between the upstream pressure tap (54) and the intermediate pressure tap (55). This adjustment of the manual valve to set the differential pressure across the differential pressure-regulating valve range optimizes the throttling capability of the differential pressure-regulating valve.

The minimum requirements for a wellhead consists of a section of piping with a valve (50), used for manual flow regulation and shut-off, and a sample collection port (60) with a shut-off valve for obtaining gas samples to determine the gas composition. The present invention adds to this an automatically controlled differential pressure-regulating valve (52); three pressure sensing taps, the upstream pressure tap (54), on the gas well side of the pressure-regulating valve, the intermediate pressure tap (55) between the pressure-regulating valve and the manual flow regulating and shut-off valve, and the downstream pressure tap (56), located downstream of the manual valve (50); a temperature sensor (58) upstream of the differential pressure regulating valve; a control circuit (64); and a data port (66).

Figure 3A:
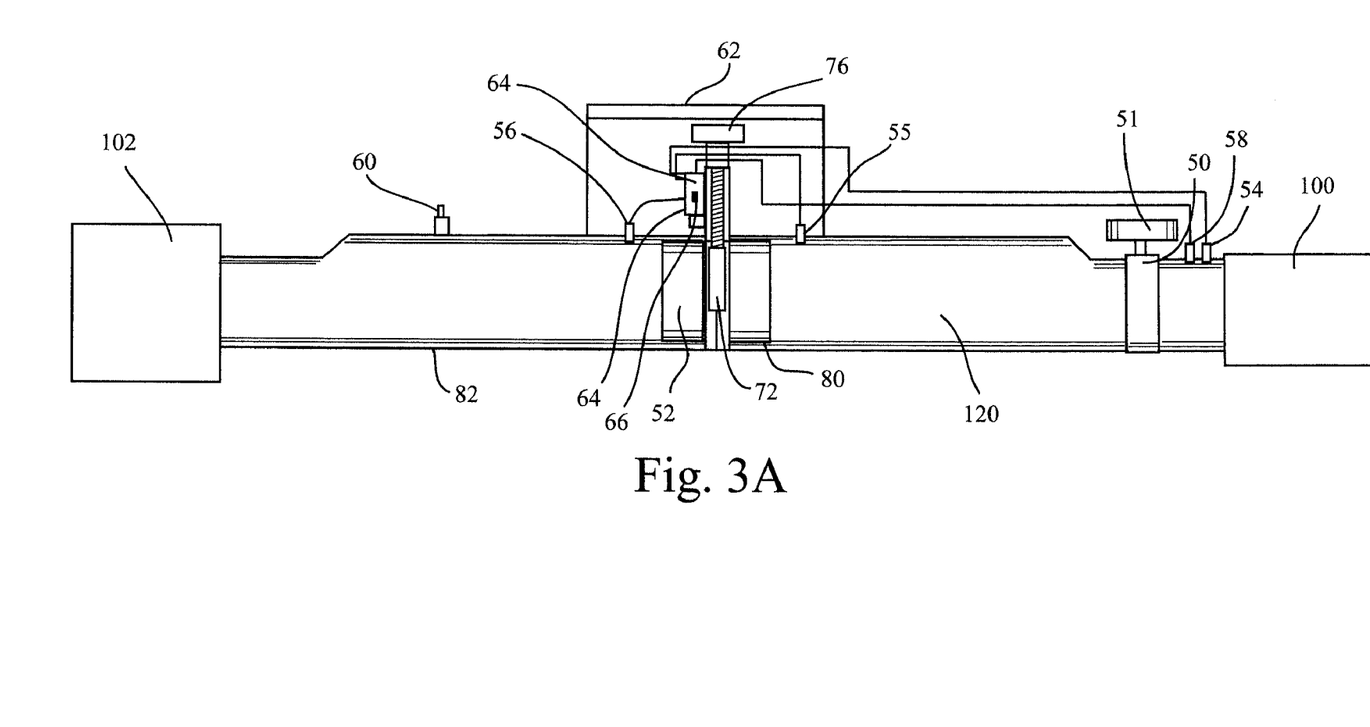
FIGS. 3A and 3B show alternative arrangements of the assembly pressure measurement taps.

In FIG. 3 and FIG. 3A the box (100) is the well extraction pipe coming from the landfill wells, previously described, and it depicts the flow from the landfill to the wellhead assembly, and is also called the upstream direction. The box (102) is the pipe to the well extraction vacuum source, previously described, and it depicts the flow from the wellhead assembly, and is also called the downstream direction.

The valve used for manual flow adjustment and shut-off (50) is used by the constant flow control wellhead to establish an initial desired differential pressure across the differential pressure regulating valve by throttling the vacuum applied to the wellhead differential pressure-regulating valve. This valve is in a fixed position during normal operation, and is used only during periodic flow adjustments.

Figure 4:
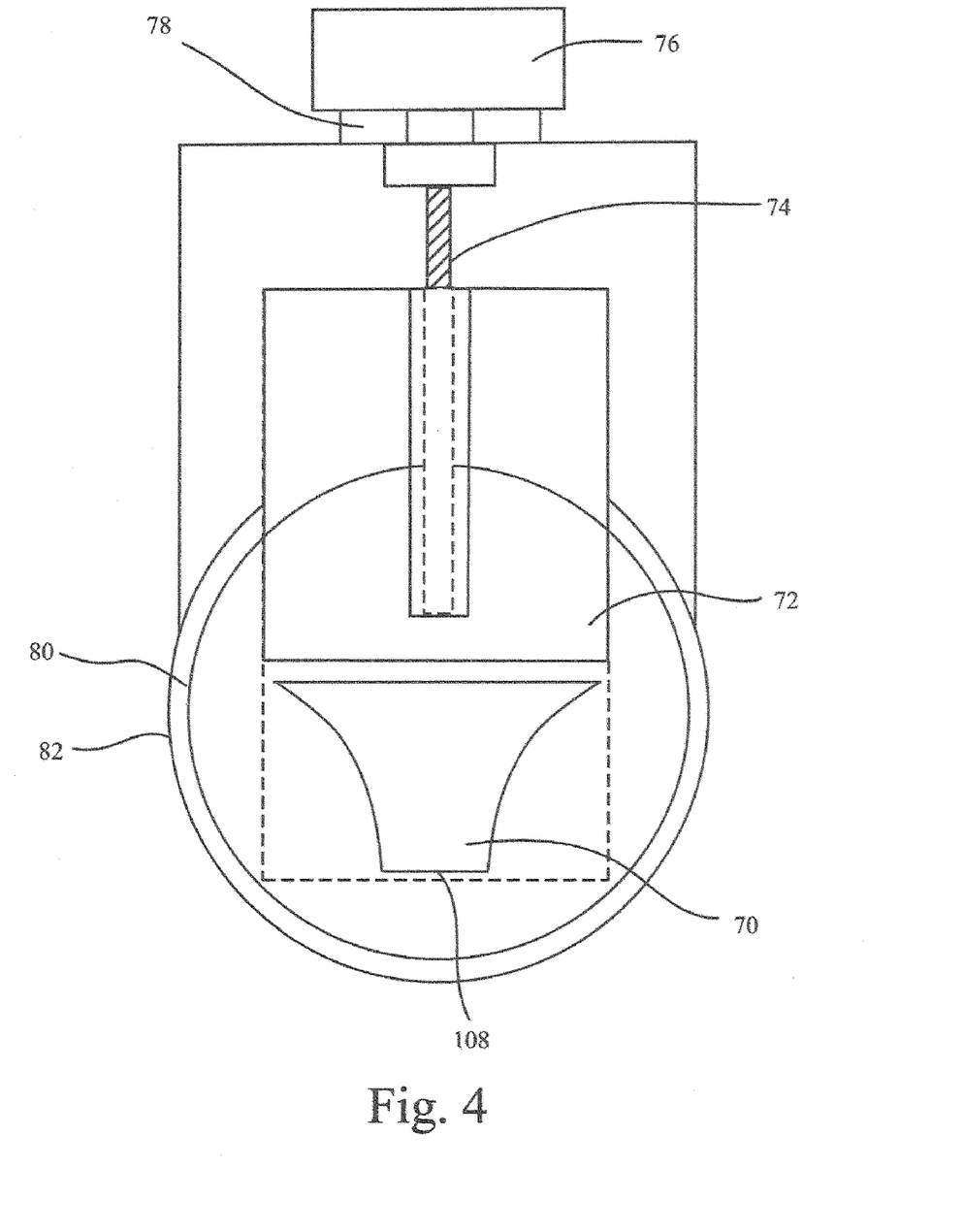
FIG. 4 is a schematic of the differential pressure-regulating valve.

The differential pressure-regulating valve (52), shown in more detail in FIG. 4, is a gate valve with a geometrically pre-determined valve opening area that provides a linear change in differential pressure with a change in valve flap position. The term linear is used to describe a change that approximates a straight line when the effect of variations in one parameter (example area) is graphed against a second parameter (example differential pressure). The flow area (70) portion of the valve is shaped as shown in FIG. 4. The valve flap moves in a channel integrally cast in the valve body (80). The differential pressure-regulating valve is designed to initiate operation with a differential pressure of 2.0 inches WC, and each position of the valve flap will represent a unique flow rate, from fully open, which opens the entire flow area to flow, to nearly closed, which allows flow only through the narrowest bottom portion of the flow area. The flow area (70) optimizes the flow control as the shape of the opening was calculated to provide a linear response between a change in valve flap position and the resulting change in differential pressure.

The shape of the differential pressure-regulating valve flow area is derived through manipulation of the orifice flow meter equation, which is derived from the Bernoulli and Continuity Equations. The orifice flow meter equation is as follows:

$$Q = KA_o \sqrt{\frac{2g(\gamma_m - \gamma_{lfg})\Delta h_m}{\gamma_{lfg}}}$$

Where:
Q=Flow Rate
$A_O$=Cross Sectional Area of Orifice
K=Discharge Coefficient
g=gravitational acceleration constant
γ=specific weight
Δh=differential pressure, measured as head
m subscript denotes manometer fluid characteristics
lfg subscript denotes landfill gas characteristics When the orifice flow meter equation is re-arranged and the flow rate is held constant and other parameters are specified, a relationship between the cross sectional area of the orifice and the differential pressure (DP) measured across the orifice can be defined. This relationship defines a range of pair values of cross sectional area and DP that are possible for the given flow rate. This relationship is as follows:

$$A_o = \frac{Q}{K\sqrt{\frac{2g(\gamma_m - \gamma_{lfg})\Delta h_m}{\gamma_{lfg}}}}$$

This equation is plotted in FIG. 1 for the flow rate of 20 standard cubic feet per minute (scfm).

The Discharge Coefficient, K, is a function of approach geometry and the Reynolds Number (a measure of flow characteristic). In designing the valve flow area, an assumed discharge coefficient was initially used. The initial design of the flow area was constructed and subsequently tested. A discharge coefficient was determined through specific calibration testing of the initial flap opening design. The fluid dynamic testing of the flow area revealed that the discharge coefficient changed as the flap was raised in elevation. This information was used in developing the final design of the flow area.

Considering the magnitude of pressures that are typically encountered in landfill gas extraction wells, the units of pressure measurement that was selected for Dhm is inches water column (WC), which is pressure expressed as head. The manometer fluid is therefore water and the characteristics of water at standard conditions for measurement were utilized in the equations presented above.

The specific weight of landfill gas, γ, was estimated by determining the weighted average of methane, carbon dioxide and nitrogen specific weights. Each constituent of landfill gas was weighted by the concentration it typically has in extracted landfill gas.

The procedure for calculating the flap opening geometry proceeded in a step-wise fashion. One set of calculations was performed for each selected flow rate. The selected flow rates ranged from 1 to 50 scfm. Once a flow rate was selected, the calculations proceeded with determining the cross sectional areas required for differential pressures (DP) in the range of 0 to 4.0 inches WC for the selected flow rate. This results in a curve of values similar to the value seen in FIG. 1. The range of DP between 1 and 4.0 has a strong linear relationship with the change in required cross sectional area of the flap opening. Also, this range of DP values produces the greatest change in cross sectional area for a given change in DP.

A rectangular opening was designed for the flow rates ranging from 0 to 5 scfm to provide the required cross sectional area. The width of the flap opening was increased with height for flow rates above 5 scfm to provide the required cross sectional area for the given flow. The flap opening width for each given flow rate was determined by reiteratively selecting a width until a width was found that could yield a "workable" flap elevation change per 0.1 inch WC DP change.

The stepper motor (76), shown in FIGS. 3, 4, and 5A, controls the differential pressure regulating valve flap position. The stepper motor, as shown in FIG. 4, is connected to and rotates a valve stem (74). The stem has male threads along its length on the end in contact with the valve flap (72), and the threads mate with female threads in the valve flap opening that receives the valve stem. The flap is constrained from rotation by the valve body channel in which it is located, so rotation of the stem causes the flap to move up or down depending on the direction of the stem rotation. An alternative valve configuration may use a stem that moves up and down with the valve flap in response to rotation of a nut connected to the stepper motor. An integral valve flap position sensor (78) is incorporated in the valve. The valve body and bonnet (80) is cast in two pieces with the restricted flow area (70) cast integral with each half. Each half has a valve flap channel on the mating side in which the valve flap can move up and down. The two halves are assembled together with the valve flap and then the body assembly is attached to the control section of piping (82).

The piping (82) adjacent to the automatically controlled differential pressure valve (52), as shown in FIGS. 3 and 5A, contains an upstream pressure measurement tap (54) upstream of the valve, an intermediate pressure measurement tap (55) downstream of the valve, and a downstream pressure measurement tap (56) downstream of the manual flow regulating and shut-off valve. Sensors in the control circuit (64), with inputs and outputs shown in FIG. 5B, measure these pressures and the difference in pressure is calculated from these measurements to yield the differential pressure across the differential pressure-regulating valve and the differential pressure across the complete wellhead assembly gas path. These differential pressures may be displayed using the data port in the control circuit. There also is a temperature sensor (58) upstream of the valve. This signal is also transmitted to the control circuit. Another tap is used as a sample collection port (60).

Figure 2:
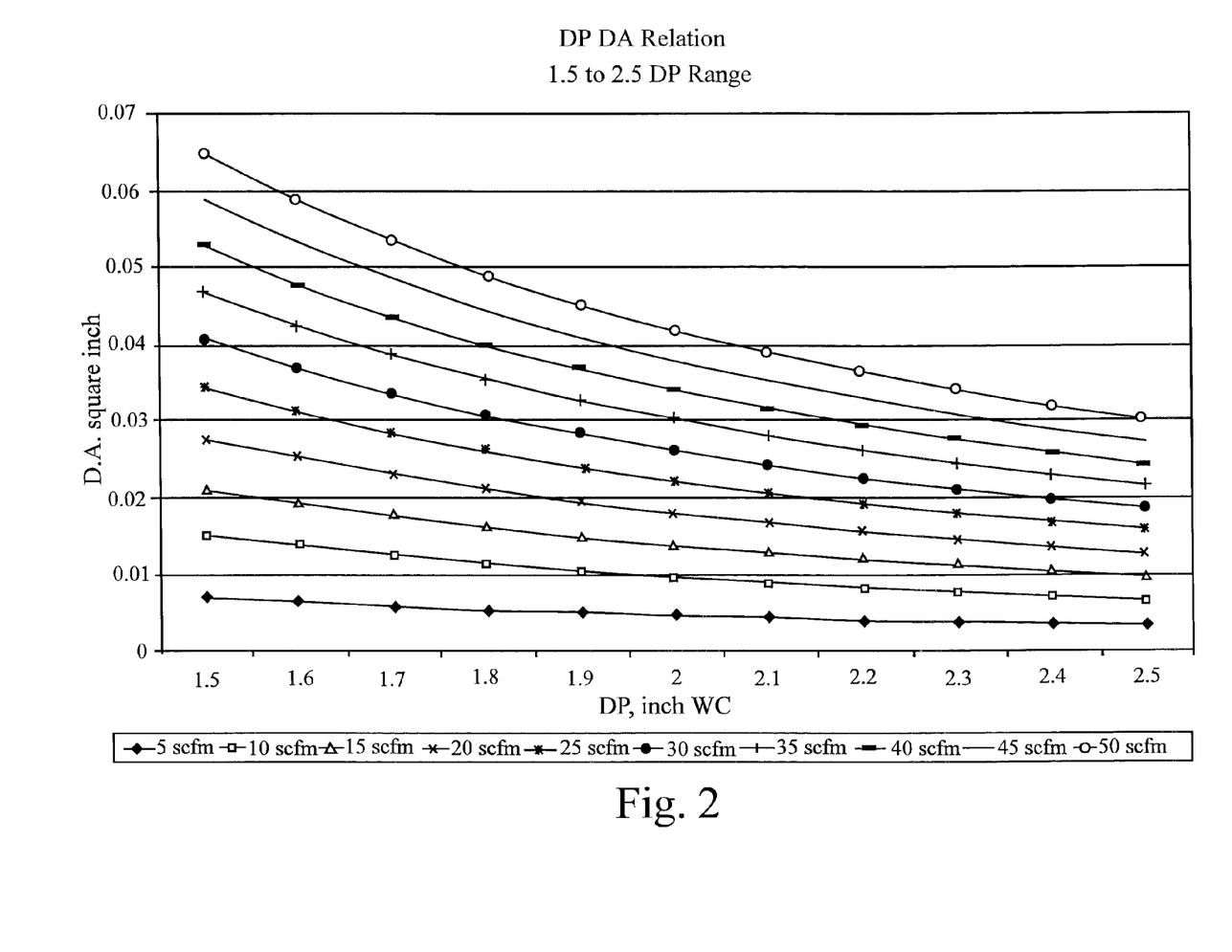
FIG. 2 shows curves of the differential pressure regulating valve differential pressure versus differential area for flow rates of 5 to 50 scfm.

The control circuit (64) is battery (106) powered in the preferred embodiment, but may be powered from external sources. The circuit drives the regulating valve stepper motor (76) to position the regulating valve based on any measured deviation from the differential pressure setpoint, which is the differential pressure equivalent to the entire flow through the wellhead assembly after the desired flow rate has been established. The control algorithm for this is simple as the regulating valve flow area (70), shown in FIG. 4, is shaped to provide a linear, or constant, change in differential pressure for a given valve flap movement over the entire range of valve travel. This linear relationship is shown for the preferred differential pressure range of 1.5 to 2.5 inch WC in FIG. 2. The control circuit is normally in a dormant state and approximately every 10 minutes will go to an active state where the differential pressure value is sampled and processed by averaging the values over time to account for fluctuations in the measurements, and to allow rounding the average. If needed, the control then produces increments of valve movement proportional to any deviation of the average differential pressure from the differential pressure setpoint, and then it returns to the dormant state.

The upstream gas temperature sensor (58), that provides a temperature input to the control circuit, is used with clock time to provide a data set of time and temperature. If the temperature exceeds the operator-selected shutdown setpoint value the control circuit will close the regulating valve.

Figure 5B:
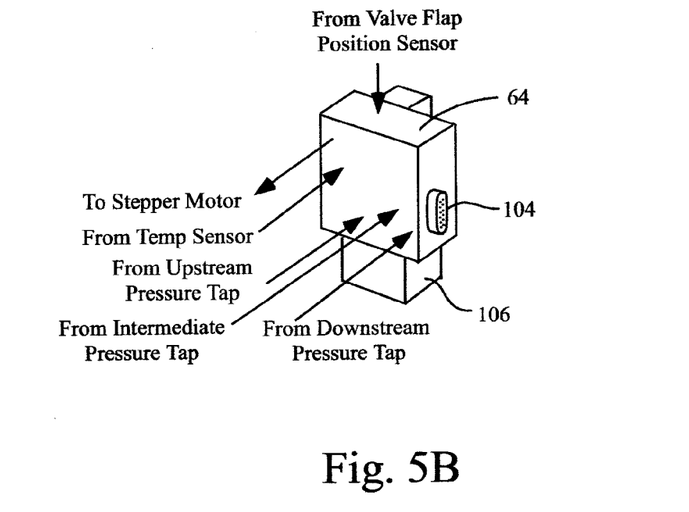
FIG. 5B is an isometric view of the control circuit. It includes descriptive legends to show the inputs and outputs used for the methane gas extraction constant flow control wellhead assembly control.

Federal regulations (40 CFR 755 and 756) require monthly measurement of the temperature of the landfill gas and the gauge pressure at each well. FIG. 5B shows the data port (106) on the control circuit that provides the display capability, using a portable hand-held computing device such as a personal digital assistant (PDA). The control circuit provides the temperature and pressure data handling through the data port. The portable hand-held computing device is used to adjust the differential pressure setpoint that the control circuit uses for positioning the regulating valve, and the temperature setpoint used to shutdown the well. The control circuit also provides information on battery status and the status of the control circuit, its sensors, and the stepper motor. It also may provide power to warning devices in the event of such conditions as low battery voltage or high gas temperature.

ALTERNATE EMBODIMENTS

The pressure-regulating valve position in the flow path may be varied if needed to accommodate existing installation configurations. The manual valve may be placed in the flow path upstream of the pressure-regulating valve. In this case, the pressure taps will be placed upstream of the manual valve, between the manual valve and the pressure-regulating valve, and downstream of the pressure-regulating valve as shown in FIG. 3A. The differential pressure across the pressure-regulating valve is then measured using the intermediate pressure measurement tap (55) and the downstream pressure measurement tap (56) in this configuration. The differential pressure across the complete wellhead gas path is still measured by the upstream pressure measurement tap (54) and the downstream pressure measurement tap (56) as shown in FIG. 3A.

Improved stability of the well flow rate is obtained by using the signal from the temperature sensor to also compensate for the change in density of the landfill gas with temperature variations, such as might occur with a diurnal variation and with longer term variations, such as occur with the changing seasons. The control circuit makes the density correction when determining if a deviation from the differential pressure setpoint exists. The gas pressure varies with the gas density and temperature according to the following form of the ideal gas equation of state:

$$P = \rho RT$$

and:

$$\rho = \frac{P}{RT}$$

Where:
=Pressure
R=Universal Gas Constant
T=Temperature (in absolute scale, Rankine or Kelvin)
$\rho$=Density The gas constant and the pressure do not change the density significantly for purposes of this control system. Therefore the density is inversely proportional to the temperature.

When using density correction, the control circuit determines the setpoint value by multiplying the absolute temperature times the differential pressure across the complete wellhead assembly gas path, which is proportional to the entire flow from the well(s). This setpoint differential pressure is that which is input by the operator using the PDA to obtain the desired differential pressure across the differential pressure-regulating valve. When the control circuit monitors the differential pressure equivalent to the entire flow through the complete wellhead assembly gas path, the circuit divides the setpoint value by the current gas temperature to determine the required differential pressure to maintain a constant flow rate, and compares this required differential pressure to the current differential pressure equivalent to the entire flow from the well(s) to determine if a deviation exists. If needed, the control circuit then produces increments of differential pressure-regulating valve movement proportional to the deviation.

Figure 3B:
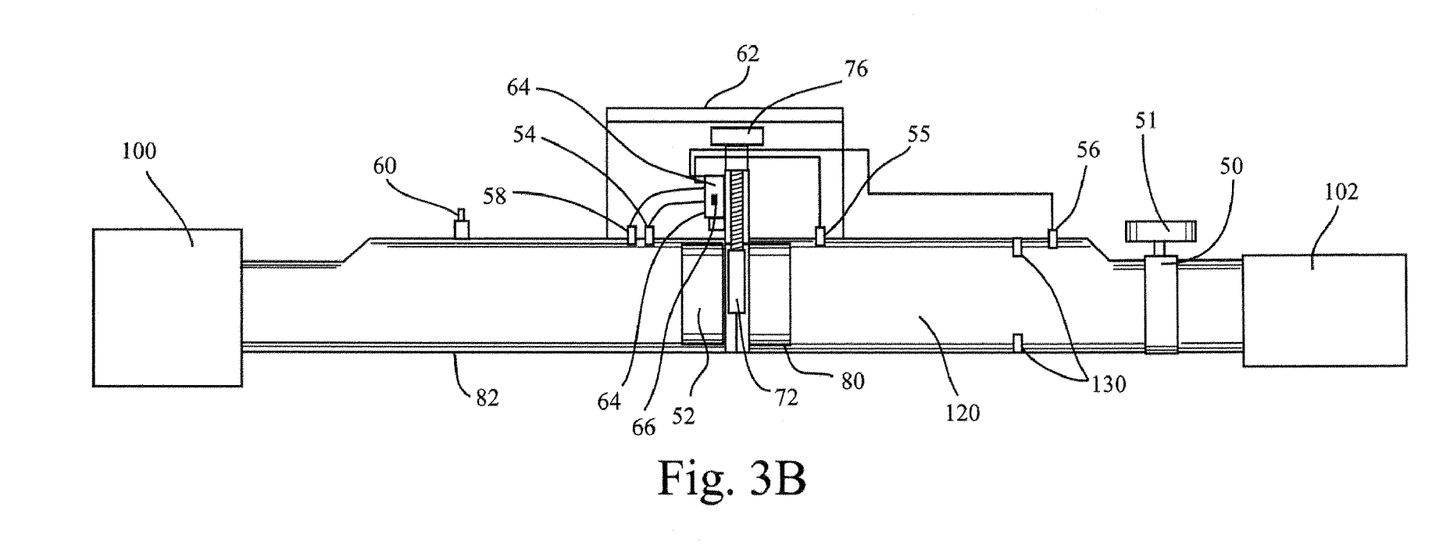

An alternative flow rate measurement equivalent to the entire flow from the well(s) may be obtained by installing a flow measurement device (130) as shown on FIG. 3B. The downstream pressure measurement tap (56) is then located downstream of the flow measurement device. The flow measurement device may be any device to create a differential pressure for flow measurement purposes (example an orifice plate, a venturi, a piping direction change, etc.). With the flow measurement device, the control circuit uses the differential pressure between the intermediate pressure measurement tap (55) and the downstream pressure measurement tap (56) to determine the flow rate equivalent to the entire flow through the wellhead assembly. This flow rate is equivalent to the flow rate obtained by measuring the differential pressure across the complete wellhead assembly gas path in that it indicates the entire gas flow rate from the well(s). The upstream pressure measurement tap (54) and intermediate pressure measurement tap (55) are still used for measuring the differential pressure across the differential pressure-regulating valve (52) in this embodiment.

OPERATION

This method of landfill gas extraction control using the constant flow wellhead has four operating modes: normal operation, data acquisition to meet well monitoring requirements, flow adjustment to compensate for longer term changes in gas extraction rate, and periodic calibration of the instrumentation.

Startup following installation of the constant flow control wellhead requires checking for closure of the manual flow regulating and shut-off valve, establishing battery power to the wellhead, and then disabling the control circuit differential pressure monitoring using a personal digital assistant (PDA) attached to the data port. The differential pressure-regulating valve is then positioned using the same data port connection at a nominal position established by experience with the optimal flow rate from the well. The manual flow regulating and shut-off valve is then opened to establish flow from the well as the real-time differential pressure reading is monitored on the PDA. The manual flow regulating and shut-off valve is then set to a position by turning the handle to establish a differential pressure near the desired value of 2 inches WC across the differential pressure-regulating valve.

Once the 2-inch WC differential pressure is established across the differential pressure-regulating valve, the differential pressure across the complete wellhead assembly is measured and this measured value is entered into the control circuit as the control setpoint using the PDA.

The control circuit is then placed in the normal operation mode. Normal operation is to maintain a constant flow rate from the well by monitoring and maintaining the differential pressure across the complete wellhead assembly. Periodically the control circuit will activate to monitor and process the differential pressure measurements and adjust the regulating valve flap height as needed to maintain a constant differential pressure.

Monthly, or more frequently if desired, the extraction well will be manually monitored. Monitoring is required by federal regulation (40 CFR 756) to include collection of a sample of landfill gas using the sample port on the wellhead. A PDA is connected to the data port and used to place the control circuit in the data acquisition mode. In this mode the gas temperature and gage pressure is measured as well as regulating valve flap position. The well flow rate is derived from the differential pressure across the entire wellhead assembly by a conversion provided in the PDA software. The PDA is used to transfer this data and the well identification to a permanent record.

The gas sample is analyzed to determine its composition and the results used to determine if the composition indicates the present flow rate from the well is resulting in over or under extraction. If a change in flow rate is indicated by the gas analysis results, the flow rate from the well is adjusted.

The flow rate of the wellhead assembly is changed using the PDA to place the control circuit in the flow adjustment mode. This suspends the monitoring and differential pressure maintenance of the normal operating mode and permits commands from the PDA to position the regulating valve flap. The regulating valve flap location is then adjusted open if the well is under-extracted, or closed if the well is over-extracted. The PDA display shows the changes in differential pressure across the differential pressure-regulating valve as this valve is adjusted.

Following adjustment of the regulating valve flap elevation, the desired differential pressure across the regulating valve of approximately 2 inches WC is re-established by adjusting the manual flow regulating and shut-off valve. Once the desired differential pressure is attained across the regulating valve, the differential pressure equivalent to the entire flow through the wellhead assembly is measured and entered as the new control set point. At this point, the flow adjustment mode is suspended and the monitoring mode is re-established.

Periodically the pressure sensors-will require a calibration check. The control circuit is placed in calibration mode using the PDA. This suspends the monitoring and differential pressure maintenance of the normal operating mode and permits attachment of a transfer pressure standard to the pressure taps. The data from the standard is compared to the control circuit readings at various regulating valve flap positions to determine the need for adjustment of the control circuit.

We claim:

1. A method of regulating landfill gas well production flow rate comprising:
   a. installing a constant flow control wellhead assembly gas path in a section of piping between each well, or grouping of wells with a single extraction pipe, and a well extraction vacuum source,
   b. opening a differential pressure-regulating valve in the wellhead assembly gas path to a nominal position,
   c. opening a manual valve in the same wellhead assembly gas path partially,
   d. measuring the differential pressure across the differential pressure-regulating valve,
   e. adjusting the manual valve position to set the desired differential pressure across the differential pressure-regulating valve,
   f. measuring the differential pressure equivalent to the entire flow through the wellhead assembly gas path,
   g. adjusting the differential pressure-regulating valve, as needed, to maintain the desired differential pressure equivalent to the entire flow through the wellhead assembly gas path,
   h. measuring the gas composition at the wellhead assembly gas path on a periodic basis, i. re-adjusting the differential pressure-regulating valve position periodically, if needed, using the result of the gas composition measurement to determine the desired direction of adjustment,
j. measuring the adjusted differential pressure across the differential pressure-regulating valve,
k. adjusting the position of the manual valve to obtain the desired differential pressure across the differential pressure-regulating valve,
l. measuring the adjusted differential pressure across the complete wellhead assembly gas path, and
m. adjusting the regulating valve, as needed, to maintain the desired differential pressure across the complete wellhead assembly gas path.

2. The method of claim 1 further comprising adjusting the manual valve position to set the differential pressure-across the regulating valve within a range of 1 to 4 inches WC.

3. A landfill gas well extraction control system comprising:
a. means for opening a differential pressure regulating valve in a complete wellhead assembly gas path to a nominal position,
b. means for opening a second valve in the gas path,
c. means for measuring the differential pressure across the differential pressure regulating valve,
d. means for setting the second valve position to obtain the desired differential pressure across the differential pressure-regulating valve,
e. means for measuring the differential pressure equivalent to the entire flow through the complete wellhead assembly gas path,
f. means for maintaining the desired complete wellhead assembly gas path differential pressure at a constant value,
g. means for obtaining a sample for measuring the gas composition on a periodic basis, and
h. means for adjusting, if needed, the differential pressure equivalent to the entire flow through the complete wellhead assembly gas path.

4. A multiplicity of constant flow wellhead assemblies controlling flow through piping for a multiplicity of landfill gas extraction wells that use a common extraction vacuum source, each constant flow wellhead assembly comprising:
a. a differential pressure-regulating valve,
b. a second valve connected to the regulating valve by piping,
c. a piping connection to the vacuum source,
d. a multiplicity of pressure taps arranged such that the taps measure the differential pressure across the differential pressure-regulating valve and measure the differential pressure equivalent to the entire flow through the wellhead assembly,
e. a control circuit providing display capability of the differential pressure between the pressure taps equivalent to the entire flow through the wellhead assembly, and display capability of the differential pressure between the pressure taps equivalent to the differential pressure across the differential pressure-regulating valve, and which positions the differential pressure-regulating valve to maintain a desired flow through the wellhead assembly, and
f. a sample collection port located in the piping such that a sample of the well gas may be obtained.

5. The wellhead assembly of claim 4 further comprising the differential pressure-regulating valve is configured such that at any initial valve position an increment of valve flap motion provides the same change in differential pressure.

6. The wellhead assembly of claim 5 further comprising gas stream temperature is measured upstream of the valves and is provided to the control circuit which closes the pressure-regulating valve in the event of high temperature.

7. The wellhead assembly of claim 6 further comprising the differential pressure equivalent to the entire flow through the wellhead assembly is the difference between the pressure upstream of a flow measurement device and the pressure downstream of a flow measurement device.

8. The wellhead assembly of claim 6 further comprising the differential pressure equivalent to the entire flow through the wellhead assembly is the difference between the pressure upstream of both the pressure-regulating valve and second valve and the pressure downstream of both the pressure-regulating valve and second valve.

9. The wellhead assembly of claim 6 further comprising a battery power supply for the control circuit.

10. A constant flow control wellhead assembly for a landfill gas well extraction system comprising:
a. a manually controlled valve providing an open position, a closed position, and a multiplicity of partially open valve positions,
b. a pressure-regulating valve,
c. a multiplicity of pressure measurement taps in the piping arranged such that two taps may be used to measure the differential pressure across the pressure-regulating valve and such that two taps may be used to measure the differential pressure equivalent to the entire flow through the wellhead assembly,
d. a sample tap such that a sample of the landfill gas passing through the wellhead assembly may be obtained, and
e. a control circuit arranged such that the differential pressure across the pressure-regulating valve may be displayed to set the desired position of the manually controlled valve, and the differential pressure equivalent to the entire flow through the wellhead assembly may be displayed such that it may be used as a control parameter for the pressure-regulating valve.

11. The wellhead assembly of claim 10 further comprising the pressure-regulating valve includes a flow area and a movable flap, the flow area is configured such that at any initial valve position an increment of valve flap motion provides a linear relationship with the change in differential pressure.

12. The wellhead assembly of claim 11 further comprising the pressure-regulating valve having a range of movement from a closed position, that entirely covers the flow area, to a fully open position, that completely uncovers the flow area, and the flap has a straight lower edge, the location of the straight lower edge in the flow area defining the size of the open flow area through which fluid may traverse the valve, and the flow area having an upstream side and a downstream side, and the flow area is configured to provide the linear relationship between the difference in fluid pressure on the upstream side and on the downstream side and the position of the flap between the open and closed positions.

13. The wellhead assembly of claim 12 further comprising the pressure-regulating valve is positioned by a signal generated by the control circuit.

14. The wellhead assembly of claim 13 further comprising gas stream temperature is measured upstream of the pressure-regulating valve and used in the electronic control circuit to close the pressure-regulating valve in the event of high temperature.

15. The wellhead assembly of claim 14 further comprising a battery power supply for the control circuit.

16. The wellhead assembly of claim 15 further comprising the differential pressure-regulating valve is directly connected to the vacuum source and the manually controlled valve is upstream of the pressure-regulating valve.

17. The wellhead assembly of claim 16 further comprising the differential pressure equivalent to the entire flow through the wellhead assembly is the difference between the pressure upstream of a flow measurement device and the pressure downstream of a flow measurement device.

18. The wellhead assembly of claim 17 further comprising the differential pressure equivalent to the entire flow through the wellhead assembly is the difference between the pressure upstream of both the manually controlled valve and pressure-regulating valve and the pressure downstream of both the manually controlled valve and pressure-regulating valve.

* * * * *